United States Patent
Vezzani

(10) Patent No.: US 6,416,585 B1
(45) Date of Patent: Jul. 9, 2002

(54) METHOD FOR CRYSTALLIZING POLYOLS AND SUGARS

(75) Inventor: Corrado Vezzani, Milan (IT)

(73) Assignee: Vomm Chemipharma S.r.l., Milan (IT)

( * ) Notice: Subject to any disclaimer, the term of this patent is extended or adjusted under 35 U.S.C. 154(b) by 97 days.

(21) Appl. No.: 09/628,509

(22) Filed: Jul. 28, 2000

(30) Foreign Application Priority Data

Jul. 30, 1999 (IT) .......................................... MI99A1721

(51) Int. Cl.$^7$ ................................................. C13F 1/02
(52) U.S. Cl. .......................................... 127/60; 568/868
(58) Field of Search ............................. 127/60; 568/868

(56) References Cited

U.S. PATENT DOCUMENTS

| | | | |
|---|---|---|---|
| 3,513,023 A | * 5/1970 | Kusch | ........................... 127/58 |
| 3,879,173 A | 4/1975 | De Vries et al. | |
| 4,620,880 A | * 11/1986 | Bodele et al. | ................ 127/60 |
| 5,980,640 A | * 11/1999 | Nurmi et al. | ................ 127/60 |
| 6,206,977 B1 | * 3/2001 | Nurmi et al. | ................ 127/15 |

FOREIGN PATENT DOCUMENTS

| | | | |
|---|---|---|---|
| EP | 0 330 352 | | 8/1989 |
| EP | A-0538653 A | * | 4/1993 |
| EP | 0 542 131 | | 5/1993 |
| EP | 0 710 670 | | 5/1996 |
| EP | 0 885 864 | | 12/1998 |
| EP | 1 008 602 | | 6/2000 |
| GB | 1 287 509 | | 8/1972 |
| GB | 1 481 846 | | 8/1977 |
| GB | 2 046 743 | | 11/1980 |

* cited by examiner

*Primary Examiner*—David Brunsman
(74) *Attorney, Agent, or Firm*—Sughrue Mion, PLLC

(57) ABSTRACT

A method for the continuous crystallization of sugars or polyols, comprising the steps of:

arranging in a thin, turbulent and dynamic layer a continuous flow of melted mass of a compound selected among the group comprising sugars and polyols, with at least 98% of dry material, and a mass of said compound in crystalline form as a crystallization seed;

advancing said thin layer of material along a cooling wall at a temperature between −15° C. and +5° C.;

granulating the material while said thin layer is advanced along the cooling wall, thus obtaining granules of the crystallized compound, and cooling said granules to room temperature, after a predetermined maturation time.

7 Claims, 1 Drawing Sheet

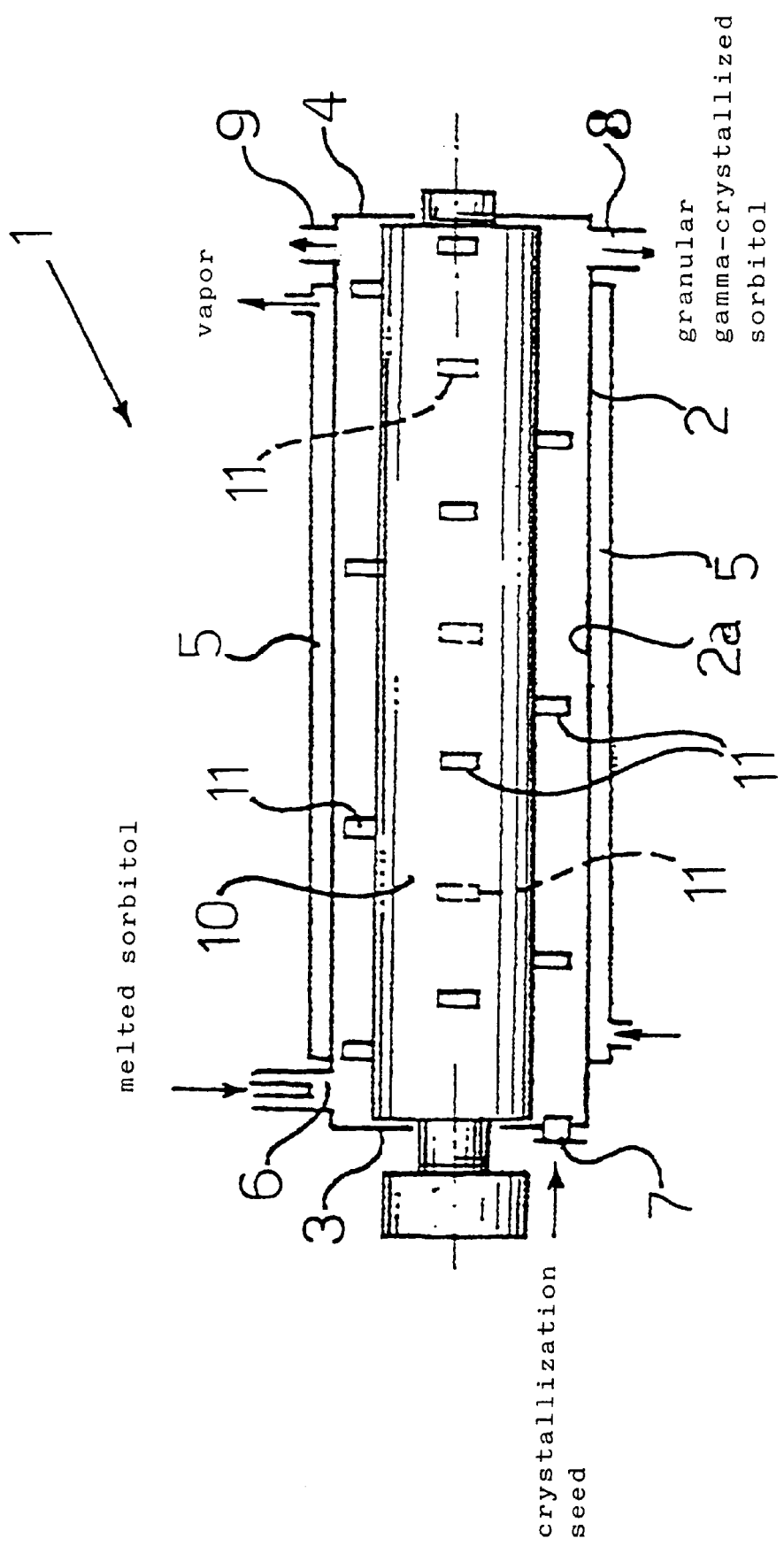

METHOD FOR CRYSTALLIZING POLYOLS AND SUGARS

FIELD OF THE INVENTION

The present invention relates to a method for crystallizing sugars and polyols, in particular with reference to sorbitol. The invention also relates to the crystallized sorbitol obtained with such a method.

The following description mainly concerns a method for the crystallization of sorbitol, since, among all the sugars and polyols compounds, sorbitol is the one which implies the greatest technical difficulties as far as crystallization is concerned.

TECHNICAL BACKGROUND

Sorbitol has been broadly used as a plasticizer and a filler in many products of the pharmaceutical and confectionery industry, where nowadays is used as a sweetener or as an excipient which "aids" the tableting of the powder formulations containing it.

Because of its high hygroscopicity, sorbitol must be crystallized at a crystallization degree of at least 80% and must be preferably in the (gamma) crystallization form in order to be used in the above mentioned fields.

As it is known, sorbitol is usually obtained through catalytic hydrogenation of glucose, at the end of which, it is in the form of a highly viscous melted mass (or magma) with a concentration of about 70–72% of the dry material.

In order to be crystallized in the desired form, the thus obtained sorbitol must be concentrated up to values of 99÷99.7% of dry material, values at which sorbitol maintains the starting form of melted (or magma).

In order to prepare sorbitol with a high degree of crystallinity, the procedure usually implies cooling the melted and hot sorbitol mass, after adding a suitable quantity of sorbitol crystals or seeds.

During the cooling, the melted mass of sorbitol is usually kept under constant mixing.

The crystallized sorbitol is then subjected to fine crushing and to screening.

Despite the high degree of crystallization, the obtained sorbitol shows the disadvantage of a poor flowability and the tendency to pack when it is subjected to pressure, thus causing problems when the formulations which contain such sorbitol must be tableted.

According to improved techniques of the above mentioned method, the crystallized sorbitol melted mass is cold extruded and in such a way a higher degree of crystallization and a product more suitable for tableting are obtained.

But this technique shows an acknowledged control difficulty for a desired uniformity in the treatment of the sorbitol mass and, therefore, gives rise to a non-constant quality in the final product.

Furthermore, if the extrusion conditions are exasperated or if they are not controlled within a close range of experimentally predetermined values, a vitrification of the product can occur at a certain degree, with a subsequent qualitative decay of such a product and with a reduction of the already low flowability.

Another broadly used technique is substantially based on a batch, prolonged treatment, characterized by a slow mixing of the sorbitol melted mass plus crystallized sorbitol added as a seed, in big mixers appropriately equipped (marl treatment).

Besides the problems related to a batch production, this technique shows the acknowledged inconvenience of the cross contamination. The seriousness and the frequency with which such a contamination occurs make compulsory a thorough cleaning of the mixers at the end of each operative phase, in order to prevent fermentation processes, which would be otherwise inevitable.

SUMMARY OF THE INVENTION

The problem underlying the present invention is that of providing a method for a continuous crystallization of sorbitol, which enables to obtain sorbitol with a high degree of crystallization (or with great amounts of crystallized gamma-sorbitol), overcoming all the disadvantages mentioned with reference to the prior art, and also enabling the crystallization of other polyols and sugars.

According to the invention, this problem is solved by the method in accordance with claim 1.

For the steps of formation of the thin layer and of granulation of the material which forms such a layer, an apparatus manufactured by VOMM IMPIANTI E PROCESSI S.R.L. of ROZZANO (Milan) is advantageously used. This apparatus is available on the market with the name TURBOCRYSTALLIZER and includes a cylindrical tubular body, which is closed at its opposite ends by respective end walls and has an inner wall kept at a prefixed temperature by means of a jacket formed in the cylindrical body, a powered rotating shaft, which extends axially in said cylindrical body and is rotatably supported by its opposite end walls, said shaft being provided with radial blades, which are helically arranged and extend nearly up to said inner wall, at least an inlet opening for a flow of material to be treated and at least an outlet opening for the obtained product.

For the sake of clarity and conciseness, such an apparatus will be named turbocrystallizer in the following description and claims.

When the above apparatus is used, the method of the present invention comprises the steps described in claims 2–8.

With particular reference to the production of crystalline sorbitol, the method according to the present invention comprises the steps of feeding a first flow comprising melted sorbitol with at least 99% of dry material and a second flow of crystallization seed consisting of crystallized sorbitol, in a turbocrystallizer having the inner wall thermostated at a temperature comprised between −15° C. and 5° C., and having a bladed shaft rotating at a speed of 400–1200 r.p.m.;

intimately mixing said flows, by simultaneously centrifuging them against said thermostated wall, with the formation of a turbulent, tubular, thin layer;

advancing said thin layer along said thermostated wall with simultaneous and continuous granulation of the mixture of said flows, forming said layer;

discharging a continuous flow of crystallized granular sorbitol from said turbocrystallizer, and cooling to room temperature said granular sorbitol after a prefixed maturation time.

Advantageously, the above-mentioned flows are fed in the turbocrystallizer in a independent way one from the other.

The weight ratio between said crystallization seed (crystallized sorbitol) and said melted sorbitol entering the turbocrystallizer, is comprised in the range between 3:1 and 0.5:1 and preferably between 1.5:1 and 1:1.

The obtained granular sorbitol was shown by analysis to contain more than 95% crystallized gamma-sorbitol.

This result is surprising if it is considered that the residence time in the turbocrystallizer varies between 20 and 120 seconds and it is mainly due to the basic idea of operating (mixing, crystallizing, granulating) in a thin layer.

A further and even more surprising result consists in that each sorbitol granule shows an outer surface having a "vitrified" physical aspect, even though it is completely crystallized in the gamma form, as repeated tests have demonstrated.

This unexpected physical characteristic of the crystallized gamma-sorbitol of the present invention implies a double advantage in comparison with the prior art: a remarkable flowability and a substantial reduction, or even a complete cancellation, of the tendency to pack also when it is subjected to remarkable pressures. All this provides an increased suitability for tableting operations.

Advantageously, the melted sorbitol is fed in the turbocrystallizer at a temperature comprised in the range 85° C.–120° C., while the crystallization seed (crystallized sorbitol) is fed at room temperature.

The melted sorbitol is preferably obtained directly from the concentration phase of sorbitol produced by catalytic hydrogenation of glucose, while the crystallization seed flow is made by a part of the crystallized gamma-sorbitol, recycled after the maturation step.

The features and the advantages of the invention will be further clarified by the following description of some exemplary embodiments of the present crystallization method.

BRIEF DESCRIPTION OF THE DRAWING

This description makes reference to the attached drawing provided for illustration purposes, in which it is schematically shown a turbocrystallizer of the above-mentioned type.

DETAILED DESCRIPTION OF THE INVENTION

In such a drawing, 1 refers overall to a turbocrystallizer comprising a cylindrical tubular body 2, closed at opposite ends by respective end walls 3,4 and provided with a jacket 5. A fluid for thermostating the inner wall 2a of said cylindrical body 2 flows through the jacket 5.

The cylindrical body 2 is provided at its end wall 3 with two inlet openings 6, 7 for two respective flows of material to be treated, while at the other end wall 4 there is an outlet opening 8 for the obtained product and an opening for discharging any vapors or gases, which are developed during the treatment.

A motorized bladed shaft 10 axially extends inside the cylindrical body 2 and is rotatably supported by its opposite end walls 3,4.

There are motor means (not shown) which can rotate said bladed shaft 10 at a speed comprised between 400 and 1200 r.p.m.

The blades 11 of said shaft 10 extend radially nearly up to the inner wall 2a, of the cylindrical body 2 and are disposed according to a single or a multi-start helicoidal arrangement.

EXAMPLE 1

A continuous flow of melted sorbitol with a concentration of 99.7% of dry material and at a temperature of 110° C., is fed into the turbocrystallizer 1, whose inner wall 2a is thermostated at +5° C., while the bladed shaft 10 is rotated at a speed of 800 r.p.m.

A second flow of crystallization seed (crystallized sorbitol) with a ratio 1:1 to the melted sorbitol flow, is continuously fed at room temperature into said turbocrystallizer 1 through the opening 7.

Immediately upon admission to the tubular body 2, said flows are "taken" by the blades 11, which mix and centrifuge such flows against the inner wall 2a.

In this condition there occurs the formation of a tubular thin layer of centrifuged material, which is pushed by the blades themselves of the shaft 10, along the inner wall 2a and in heat exchange contact therewith, towards the outlet opening 8.

During its passage through the cylindrical body 2, the material (melted sorbitol and crystallization seed) of said thin layer is constantly subjected to the mechanical and dynamic action of the blades 11, which besides keeping said material in a high turbulence condition, bring about the granulation (formation and growth of the granule) thereof.

After an average residence time of 30 seconds, granulated crystallized sorbitol starts to be continuously discharged out of said opening 8 at a temperature of about 55° C.

The analysis showed that, after a two hours long maturation, the sorbitol granules resulted to be crystallized in the gamma form for more than 95% and showed a substantially vitreous physical aspect.

Furthermore, they showed definitely improved taste and solubility in comparison with the prior art.

Advantageously, the flow of melted sorbitol with 99.7% of dry material entering the turbocrystallizser 1 comes directly from teh concentration step of melted sorbitol (concentration: 70% of dry material), which is obtained from the plants for catalytic hydrogenation of glucose.

In order to obtain the above concentration, the inner wall of the turboconcentrator is thermostated at about 150° C. and the bladed shaft is rotated at 400–1200 r.p.m., while the second flow entering said turboconcentrator consists of air at 150° C.

The crystallized gamma-sorbitol of the present invention is very suitable for tableting and meanwhile can be rolled quite easily.

EXAMPLE 2

A continuous flow of melted dextrose with a concentration of 98% of dry material and at a temperature of 92° C. is fed into the turbocrystallizer 1, whose inner wall 2a is thermostated at +6° C., while the bladed shaft 10 is rotated at a speed of 840 r.p.m..

A second flow of crystallization seed (crystallized monohydrate dextrose) with a ratio 1:1 to the melted dextrose flow, is continuously fed at room temperature, into said turbocrystallizer 1 through the opening 7.

After an average residence time of 60 seconds, granulated crystallized dextrose starts to be continuously discharged from said opening 8, at a temperature of about 28° C.

Also in this case, the flow of melted dextrose with 98% of dry material, entering the turbocrystallizer 1 comes advantageously from the concentration step of a dextrose solution with 70% of dry material, which is available on the market.

Like in example 1, in said concentration step (70% 98% of dry material), a turboconcentrator by VOMM IMPIANTI E PROCESSI is advantageously used.

In the above-mentioned concentration step, the inner wall of the turboconcentrator is thermostated at about 90° C. and the bladed shaft is rotated at 750 r.p.m., while the second flow entering said turboconcentrator consists of air at 115° C.

EXAMPLE 3

A continuous flow melted fructose with a concentration of 99.1% of dry material and at a temperature of 90° C. is fed into the turbocrystallizer 1, whose inner wall 2a is thermostated at +4° C., while the bladed shaft 10 is rotated at a speed of 840 r.p.m.

A second flow of crystallization seed (crystalline fructose powder) with a ratio 1:4 to the melted fructose flow, is continuously fed at room temperature into said turbocrystallizer 1 through the opening 7.

After an average residence time of 90 seconds, crystallized fructose starts to be continuously discharged out of said opening 8, at a temperature of about 37° C.

Also in this case, the flow of melted fructose with 99.1% of dry material, entering the turbocrystallizer 1 comes advantageously from the concentration step of a fructose solution wit 70% of dry material, which is available on the market.

Like in example 1, in said concetration step (70%→99.1% of dry material), a turboconcentrator by VOMM IMPIANTI E PROCESSI is advantageously used.

In the above-mentioned concentration step, the inner wall of the turboconcentrator is thermostated at about 160° C. and the bladed shaft is rotated at 600 r.p.m., while the second flow entering said turboconcentrator consists of air at 200° C.

I claim:

1. A method for the continuous crystallization of sorbitol, comprising the subsequent steps of:

arranging in a thin, turbulent and dynamic layer a continuous flow of material, comprising a melted mass of sorbitol with at least 99% of dry material and a corresponding mass of crystallized sorbitol as a crystallization seed;

advancing said thin layer of material along and in substantial contact with a cooling wall, maintained at a temperature comprised between −15° C. and +5° C.;

granulating said material while said thin layer is advanced along the cooling wall, thus obtaining a continuous flow of granules of crystallized sorbitol, and cooling said sorbitol granules to room temperature, after a predetermined maturation time.

2. A method for the continuous crystallization of sorbitol, comprising the subsequent steps of:

feeding a first flow comprising melted sorbitol, with at least 99% of dry material and a second flow of crystallization seed consisting of crystallized sorbitol, in a turbocrystallizer having the inner wall thermostated at a temperature comprised between −15° C. and 5° C., and having a bladed shaft rotating at a speed of 400–1200 r.p.m.;

intimately mixing said flows, by simultaneously centrifuging them against said thermostated wall, with the formation of a turbulent, tubular, thin layer;

advancing said thin layer along said thermostated wall with simultaneous and continuous granulation of the mixture of said flows forming said layer;

discharging a continuous flow of crystallized granular sorbitol from said turbocrystallizer, and cooling to room temperature said granular sorbitol after a predetermined maturation time.

3. A method according to claim 2, wherein said first and second flows are fed into said turbocrystallizer independently from one another.

4. A method according to claim 2, wherein said second flow of crystallization seed and said first flow of melted sorbitol are in a weight ratio comprised between 3:1 and 0.5:1.

5. A method according to claim 4, wherein said second flow of crystallization seed and said first flow of melted sorbitol are in a weight ratio comprised between 1.5:1 and 1:1.

6. A method according to claim 2, wherein said bladed shaft is rotated at 800–1200 r.p.m.

7. A method according to claim 2, wherein the residence time of the material subjected to treatment in said turbocrystallizer is comprised between 20 and 120 seconds.

* * * * *